(12) United States Patent
Sutton

(10) Patent No.: US 8,241,242 B2
(45) Date of Patent: Aug. 14, 2012

(54) PHACOASPIRATION FLOW RESTRICTOR WITH BYPASS TUBE

(75) Inventor: Thomas B. Sutton, Orange, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 1347 days.

(21) Appl. No.: 11/095,879

(22) Filed: Mar. 30, 2005

(65) Prior Publication Data

US 2006/0224163 A1    Oct. 5, 2006

(51) Int. Cl.
*A61M 1/00*    (2006.01)

(52) U.S. Cl. ........ 604/30; 604/22; 604/23; 604/24; 604/35; 604/131; 604/118; 604/119; 604/120; 604/137; 604/191; 604/323; 604/335; 606/4; 606/17; 606/107; 433/90; 433/91; 433/92; 433/93; 433/94; 433/95; 433/96; 128/912

(58) Field of Classification Search ........ 128/912; 604/22–24, 30, 35, 131, 118, 119, 120, 137, 604/191, 323, 335; 606/4, 17, 107; 600/73; 433/90–96
See application file for complete search history.

(56) References Cited

U.S. PATENT DOCUMENTS

| | | | | |
|---|---|---|---|---|
| 3,659,558 A | * | 5/1972 | Noorlander | 119/14.52 |
| 3,702,115 A | * | 11/1972 | Elcaness | 604/119 |
| 3,741,208 A | * | 6/1973 | Jonsson et al. | 128/204.21 |
| 3,900,022 A | * | 8/1975 | Widran | 600/105 |
| 3,902,495 A | | 9/1975 | Weiss et al. | |
| 4,065,093 A | * | 12/1977 | Phillips | 251/6 |
| 4,820,265 A | * | 4/1989 | DeSatnick et al. | 604/30 |
| 4,919,129 A | * | 4/1990 | Weber et al. | 606/42 |
| 4,957,487 A | * | 9/1990 | Gerow | 604/133 |
| 5,106,367 A | | 4/1992 | Ureche et al. | |
| 5,167,620 A | | 12/1992 | Ureche et al. | |
| 5,267,956 A | | 12/1993 | Beuchat | |
| 5,318,515 A | * | 6/1994 | Wilk | 604/30 |
| 5,344,395 A | * | 9/1994 | Whalen et al. | 604/22 |
| 5,429,601 A | | 7/1995 | Conley et al. | |
| 5,429,606 A | * | 7/1995 | Robinson et al. | 604/97.03 |
| 5,605,545 A | * | 2/1997 | Nowosielski et al. | 604/118 |

(Continued)

FOREIGN PATENT DOCUMENTS

EP    1356834 A2    10/2003

(Continued)

OTHER PUBLICATIONS

Cruise Control. www.staar.com/professional_products_cataract_phaco.html. Retrieved from www on Aug. 10, 2004.

(Continued)

*Primary Examiner* — Nicholas D Lucchesi
*Assistant Examiner* — Scott Medway
(74) *Attorney, Agent, or Firm* — Abbott Medical Optics Inc.

(57) ABSTRACT

A device for achieving high vacuum stability during phacoemulsification surgery includes a main aspiration line connected to a vacuum source which enables a fluid flow from a phacoemulsification handpiece tip to a drainage reservoir. A first tubing segment is provided in the main aspiration line along with a second tubing segment generally parallel to the first tubing section and a valve disposed in the second tubing segment regulates fluid flow through the second tubing segment in order to limit vacuum surge in the main aspiration line upon clearing of an occlusion in the phacoemulsification handpiece tip.

17 Claims, 1 Drawing Sheet

U.S. PATENT DOCUMENTS

| | | | |
|---|---|---|---|
| 5,700,240 A | 12/1997 | Barwick, Jr. et al. | |
| 5,743,871 A * | 4/1998 | Strukel et al. | 604/35 |
| 5,897,527 A * | 4/1999 | Tsukada | 604/82 |
| 6,283,974 B1 | 9/2001 | Alexander | |
| 6,511,454 B1 * | 1/2003 | Nakao et al. | 604/31 |
| 6,599,271 B1 | 7/2003 | Easley | |
| 6,629,948 B2 | 10/2003 | Rockley et al. | |
| 6,780,165 B2 | 8/2004 | Kadziauskas et al. | |
| 6,780,166 B2 * | 8/2004 | Kanda et al. | 604/31 |
| 7,347,828 B2 * | 3/2008 | Francese et al. | 600/565 |
| 2002/0019605 A1 | 2/2002 | Barrett | |
| 2002/0029006 A1 | 3/2002 | Turturro et al. | |
| 2002/0128560 A1 | 9/2002 | Urich | |
| 2003/0078591 A1 | 4/2003 | Barrett | |
| 2004/0039351 A1 | 2/2004 | Barrett | |
| 2005/0054971 A1 | 3/2005 | Steen et al. | |

FOREIGN PATENT DOCUMENTS

| | | |
|---|---|---|
| JP | 4240448 | 8/1992 |
| JP | 2001523519 A | 11/2001 |
| WO | WO 03/030717 A2 | 4/2003 |
| WO | WO 2004/108189 A2 | 12/2004 |
| WO | WO 2004/110524 A2 | 12/2004 |

OTHER PUBLICATIONS

Office Action for Japanese Application No. 2008504023 mailed Mar. 15, 2011.

Office Action for Japanese Application No. 2008504023 mailed Oct. 18, 2011.

* cited by examiner

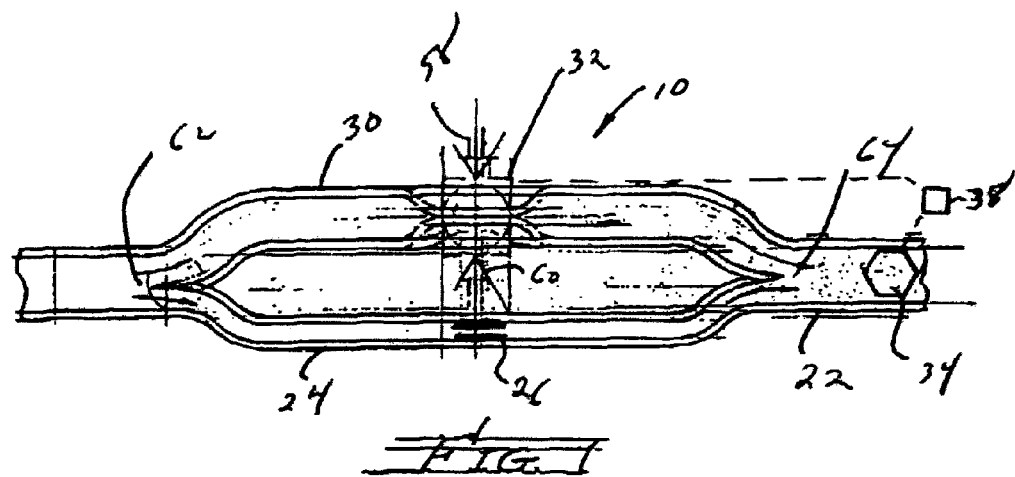
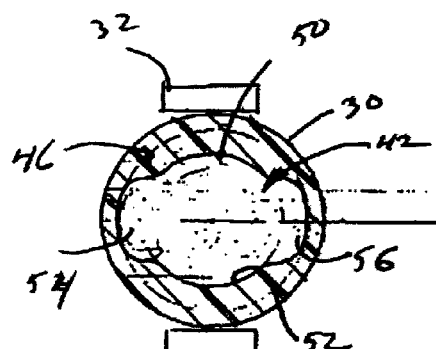 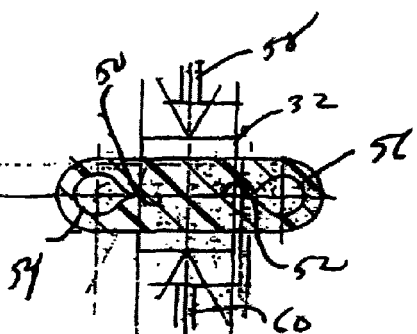

PHACOASPIRATION FLOW RESTRICTOR WITH BYPASS TUBE

The present invention generally relates to phacoemulsification surgical devices and more specifically relates to a device for achieving high vacuum stability during phacoemulsification surgery.

Phacoemulsification is a popular surgical technique for removing unwanted tissue from an eye, for example, during cataract surgery in which a diseased lens of an eye is fragmented and removed in order to be replaced with an artificial lens. A single phacoemulsification handpiece may provide for cutting and/or fragmenting the eye tissue, irrigation of the surgical site, and aspiration of the cut and/or fragmented tissue and irrigation fluids.

During any ocular surgical procedure, it is of vital importance that pressure within the eye cavity, i.e. intraocular pressure, be regulated closely in order to prevent serious injury to the patient. Excessive pressure may cause damage to fragile eye tissue. On the other hand, low levels of pressure may cause collapse of the eye cavity and rubbing between opposing surfaces thereof. Either extreme should be avoided.

Maintenance of a safe level of intraocular pressure requires close monitoring and a high level of physician competence, as there are many variables which may affect such pressure. For example, infusion of irrigation fluid to the surgical site effectively increases intraocular pressure, which must be balanced by a proper rate of aspiration of the fluids and unwanted tissue. Phacoemulsification control units for monitoring and controlling irrigation rates are utilized in conjunction with one or more phacoemulsification and/or irrigation/aspiration handpieces, and typically include, among other things, a variable speed pump, a vacuum sensor and a programmable microprocessor.

Conventionally fluid T-couplings designed for stabilizing pressure may be provided along the surgical tubing connecting the handpiece to the vacuum source. A first fluid flow channel of the T-coupling is coincident with the aspiration channel of the phacoemulsification handpiece and permits body fluids to flow from the surgical site into a drainage reservoir. A second flow channel, commonly called a vacuum vent, is connected to the phacoemulsification control unit and is provided in order to automatically release the vacuum when a predetermined vacuum level is reached.

However, despite the many monitoring and regulating devices available for use during phacoemulsification surgery, none have been satisfactory for stabilizing pressure particularly during surgery using high vacuum levels, for example, above about 300 mm Hg.

Damage to eye tissue can occur due to sudden changes in vacuum pressure, especially when high vacuum settings are being used. Blocking, or "occlusion" of the aspiration line, for example by coagulated blood or large fragments of eye tissue, will cause an increase in vacuum pressure in the surgical tubing. Simultaneously, the inflow of irrigation fluid causes intraocular pressure to build. Once the occlusion "breaks" or clears, a sudden momentary surge of vacuum, or aspiration rush, is experienced at the handpiece tip. The aspiration rush of fluid out of the eye may cause the anterior chamber of the eye to collapse because the infusion rate cannot immediately compensate therefore.

What is needed then, and what the present invention provides, is a device for achieving high vacuum stability during phacoemulsification surgery.

SUMMARY OF THE INVENTION

A device for achieving high vacuum stability during phaco surgery, particularly at high vacuum settings, generally includes a main aspiration line connected to a vacuum source and providing fluid communication, i.e. flow, from a phacoemulsification handpiece tip to a drainage reservoir.

A first tubing segment is provided and disposed in fluid communication with the main aspiration line with the first tubing segment having a bore restriction therein. The bore restriction is intended to provide resistance to aspiration flow following an occlusion break. The first tubing segment may also be considered an extension of the main aspiration line.

A second tubing segment is provided and disposed in fluid communication with the main aspiration line parallel to the first tubing segment. The second tubing segment has a bore larger than a cross section of the bore restriction in the first tubing.

Preferably, the first and second tubing segments are in fluid communication with the main aspiration line at spaced apart common junctions.

More particularly, a valve, disposed in the second tubing segment, is intended to regulate the amount of fluid allowed to bypass the bore restriction, thus regulating the amount of flow restriction in the aspiration path and limit vacuum surge in the main aspiration line upon clearing of an occlusion in the phacoemulsification handpiece tip. When in operation, the valve compresses the second tubing segment, such compression being either complete or less than complete (i.e. such that some amount of fluid can continue to pass through the second tubing segment).

Still more particularly, a vacuum sensor or a flow rate sensor may be provided and disposed in the main aspiration line which effects a valve operation when a selected vacuum level or flow rate is detected.

More specifically, the valve may comprise, for example, a pinch valve and the second tubing segment may include a profile having a cross section, including an inwardly projecting mesa with subtending channels. Alternate tubing cross sections may be utilized with the valve to regulate fluid flow. The valve may operate to partially or fully close the second tubing segment.

Still more particularly, the pinch valve may be positioned to collapse the second tubing segment by forcing opposing inside walls toward one another. A maximum valve caused collapse of the second tubing section permits flow through the subtending channels. Thus, a total blockage of the second tubing segment is not affected.

BRIEF DESCRIPTION OF THE DRAWINGS

A better understanding of the present invention may be had in reference to the following description, taken in conjunction with the accompanying drawings in which:

FIG. 1 is a diagrammatical view of a device in accordance with the present invention for achieving high vacuum stability during phacoemulsification surgery, the device being connected between a phacoemulsification handpiece (not shown) and a drainage reservoir (not shown) and including a main aspiration line and first and second tubing segments in parallel with one another;

FIG. 2 illustrates a cross sectional view of a second tubing segment in accordance with the present invention illustrating inside walls with subtending channels with a pinch clamp disposed thereabout; and FIG. 3 is a view similar to that shown in FIG. 2 with the pinch clamp causing total collapse of the inside walls while enabling subtending channels to permit fluid flow.

DETAILED DESCRIPTION

With Reference to FIG. 1, a device 10 in accordance with the present invention for achieving high vacuum stability during eye surgery, including, for example, phacoemulsification surgery, with a handpiece with a tip (not shown) and a drainage reservoir (not shown). In phacoemulsification surgery, the phacoemulsification handpiece, tip, and reservoir are conventional and not part of the present invention. Other types of eye surgery outside of phacoemulsification may also benefit from the embodiments disclosed herein, and the one or more surgical handpieces used in conjunction with these embodiments may include devices for excision, removal, movement, treatment, measurement and so on of tissue.

A device 10 generally includes a main aspiration line 22 connected to a vacuum, or aspiration, source (not shown) and enabling a fluid flow from the phacoemulsification handpiece tip to the drainage reservoir, the vacuum, or aspiration, source not being part of the present invention.

A first tubing segment 24 is provided and disposed in fluid communication with the main aspiration line 22 with the first tubing segment having a bore restriction 26 therein. As hereinabove noted, the first tubing segment 24 may be considered a continuation of the main aspiration line 22. The bore restriction 26 provides a flow area less than a flow area of the main aspiration line 22.

A second tubing segment 30 also disposed in fluid communication with the main aspiration line 22 enables diverted flow of aspiration fluid.

The second tubing segment 30 has a cross section larger than a cross section of the bore restriction 26 of the first segment 24.

More particularly, and by way of a non-limiting specific example, the total cross sectional area of the main aspiration tube may be about .0032 square inches, utilizing a 0.064 inch diameter main aspiration tube.

When utilizing a 0.02 inch diameter restriction in the first tubing segment 24, the diameter of the second tubing segment should be about 0.061 inches.

With continued reference to FIG. 1, a valve 32, for example, a conventional remotely controlled pinch valve, is disposed in the second tubing segment 30 in order to limit vacuum surge in the main aspiration line 22 upon clearing of an occlusion in the phacoemulsification tip, the occlusion not being shown. The hereinabove noted tubing cross section provides flow through the first and second tubing segment 24, 30 equivalent to flow through the main aspiration line 22 when the valve 32 is fully open. In some embodiments, the valve causes the second tubing segment to be either fully open or fully closed. In alternate embodiments, the valve is variable and can be controlled such that the second tubing section is partially closed.

In addition, a conventional vacuum pressure sensor 34 or a flow rate sensor (not shown) may be provided and disposed in the main aspiration line 22 in a conventional manner for effecting valve 32 regulation, including opening and closing, when a selected vacuum level or flow rate is detected through controller 38. Vacuum levels, flow rates and operating parameters of the handpiece and vacuum source are, of course, dependent upon the specific equipment utilized and such parameters are well known in the art.

With specific reference to FIGS. 2 and 3, an embodiment of the present invention includes a second tubing segment 30 having a profile 42 with a cross section 46 including inside walls 50, 52, or mesas, with subtending channels 54, 56.

As schematically shown, the pinch valve 32 is positioned to collapse the second tubing segment 30 by forcing the tubing inside walls 50, 52 toward one another as illustrated in FIGS. 2 and 3 by arrows 58, 60.

As also illustrated in FIG. 3, a maximum valve caused collapse of the second tubing segment 30 permits fluid flow through the subtending channels 54, 56 a cross section size of the subtending channels is typically based upon the overall cross sectional flow areas of the main aspiration line 22, the first segment 24 and the second segment 30. It should be appreciated that the second tubing segment 30 in accordance with the present invention may include various cross sections, not shown, such as, for example circular, elliptical, triangular, rectangular, polygonal or other (not shown), which in combination with a corresponding variable valve (not shown), can be used to further control the fluid flow through the second tubing segment 30. The mesa cross section 46 enables collapse, by the valve 32, to a specific shape, with channels 54, 56. Other configurations (not shown) may also be used to achieve this result.

As a specific example, the first and second tubing segments 24, 30 are in fluid communication with the main aspiration line 22 and spaced apart with common junctions 62, 64 and the valve 32 is disposed between the spaced apart common junctions 62, 64.

Although there has been hereinabove described a specific phaco aspiration flow restrictor with bypass tube in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. The various embodiments of the present invention have generally been discussed with reference to ophthalmology. However, the embodiments have equal application to other medical arts, including those in which irrigation and aspiration are used in the excision, removal, movement, treatment, measurement and so on of tissue. Accordingly, any and all modifications, variations or equivalent arrangements which may occur to those skilled in the art, should be considered to be within the scope of the present invention as defined in the appended claims.

What is claimed is:

1. A device for achieving high vacuum stability during eye surgery, said device comprising:
    a main aspiration line connected to a vacuum source and configured to enable a fluid flow from a surgical handpiece to a drainage reservoir;
    a first tubing segment disposed in fluid communication with said main aspiration line, said first tubing segment having a lumen and a bore restriction inside a portion of said lumen of said first tubing segment, wherein said bore restriction has a cross sectional flow area less than a cross sectional flow area of said lumen when said first tubing segment is fully open and uncollapsed;
    a second tubing segment disposed in fluid communication with said main aspiration line and substantially parallel to said first tubing segment, the said second tubing segment having a cross sectional flow area larger than said a-cross sectional flow area of the said bore restriction when said second tubing segment is fully open and uncollapsed; and
    a valve, disposed adjacent to said second tubing segment, and configured to control fluid flow through the said first and second tubing segments by deforming said second tubing segment to limit vacuum surge in the said main aspiration line upon clearing of an occlusion in the surgical handpiece.

2. The device according to claim 1 further comprising a vacuum sensor disposed in the main aspiration line and effecting valve operation when a selected vacuum level is detected.

3. The device according to claim 2 wherein the valve comprises a pinch valve.

4. The device according to claim 3 wherein said second tubing segment includes a profile having a cross section including inside walls with subtending channels.

5. The device according to claim 4, wherein said pinch valve is positioned to collapse said second tubing segment by forcing the inside walls toward one another.

6. The device according to claim 5 wherein a maximum valve caused collapse of said second tubing segment permits fluid flow through said subtending channels.

7. The device according to claim 1 wherein the first and second tubing segments are in fluid communication with said main aspiration line at spaced apart common junctions.

8. The device according to claim 7 wherein said valve is disposed between the spaced apart common junctions.

9. The device according to claim 8 further comprises a vacuum sensor disposed in said main aspiration line and effecting valve operation when a selected vacuum level is detected.

10. The device according to claim 9 wherein the valve comprises a pinch valve.

11. The device according to claim 10 said second tubing segment includes a profile having a cross section including inside walls with subtending channels.

12. The device according to claim 11 wherein said pinch valve is positioned to collapse said second tubing segment by forcing the inside walls toward one another.

13. The device according to claim 12 wherein a maximum valve caused collapse of said second tubing segment permits fluid flow through said subtending channels.

14. The device according to claim 1, wherein the surgical handpiece is a phacoemulsification handpiece.

15. The device of claim 1, further including a flow rate sensor.

16. The device of claim 1, wherein the second tubing segment has a circular cross-section.

17. The device of claim 1, wherein the valve operates to partially or fully collapse the second tubing segment.

\* \* \* \* \*